United States Patent [19]

Gallant

[11] 4,412,402
[45] Nov. 1, 1983

[54] EQUIPMENT AND METHOD FOR DELIVERING AN ABRASIVE-LADEN GAS STREAM

[75] Inventor: Ben J. Gallant, Portland, Tex.

[73] Assignee: Cavitron Inc., Long Island City, N.Y.

[21] Appl. No.: 197,886

[22] Filed: Oct. 17, 1980

Related U.S. Application Data

[63] Continuation of Ser. No. 65,288, Aug. 9, 1979, abandoned, which is a continuation-in-part of Ser. No. 14,435, Feb. 23, 1979, abandoned, which is a continuation-in-part of Ser. No. 928,907, Jul. 28, 1978, Pat. No. 4,174,571.

[51] Int. Cl.³ ............................................... B24C 5/04
[52] U.S. Cl. .................................... 51/439; 51/321; 433/88; 433/216

[58] Field of Search ................... 51/439, 436, 321; 433/88, 89; 128/62 A

[56] References Cited

U.S. PATENT DOCUMENTS

| 783,218 | 2/1905 | Murray | 51/43 L |
| 2,324,250 | 7/1943 | Voerge | 15/302 |

FOREIGN PATENT DOCUMENTS

| 494888 | 3/1930 | Fed. Rep. of Germany | 51/439 |

Primary Examiner—Robert Peshock
Attorney, Agent, or Firm—Vorys, Sater, Seymour & Pease

[57] ABSTRACT

Equipment for abrasive stream cleaning delivers a stream of a gas and particles and a flow of liquid. A nozzle structure provides for entrainment of the liquid by a jet of particle-laden gas.

24 Claims, 4 Drawing Figures

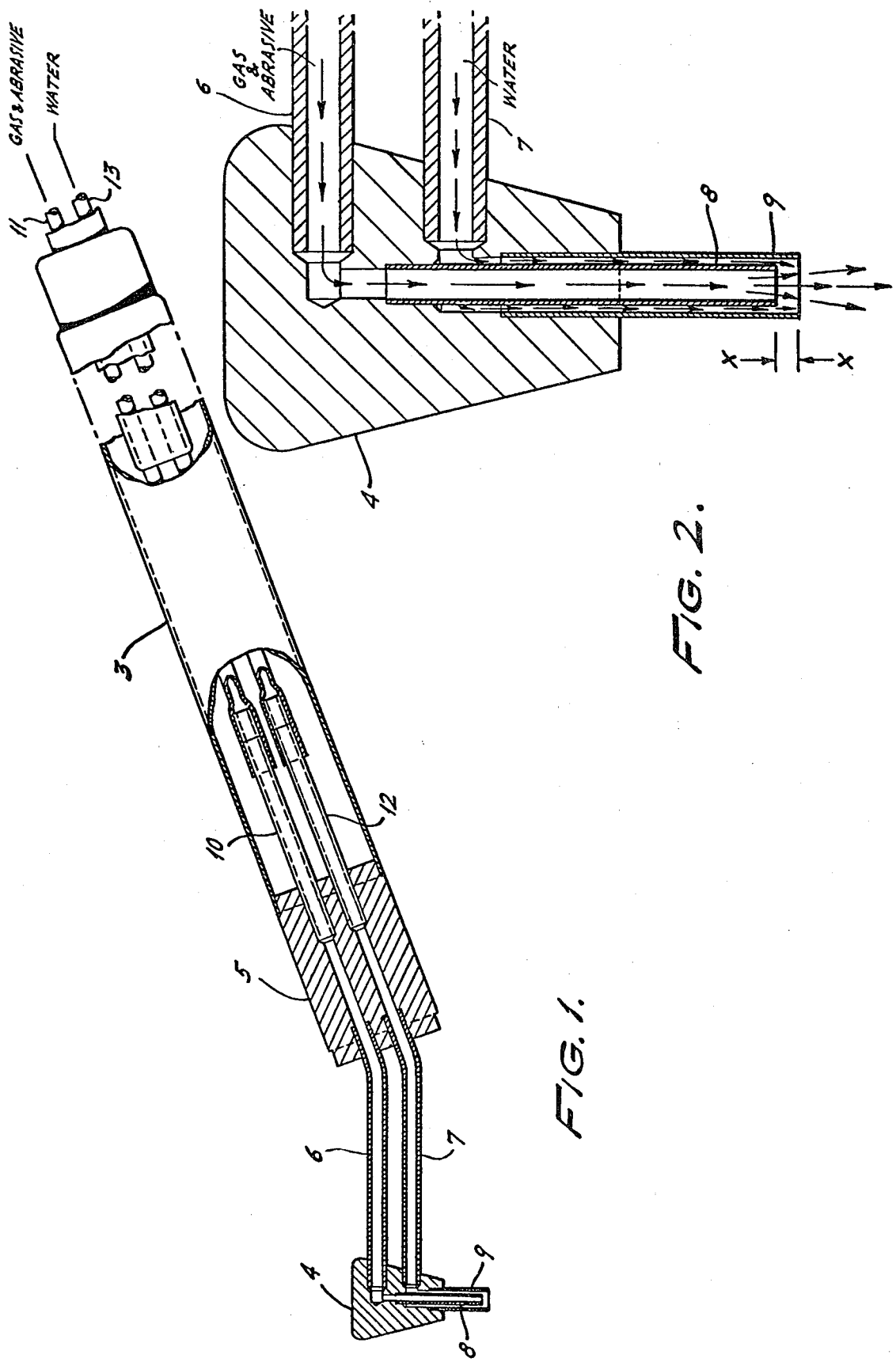

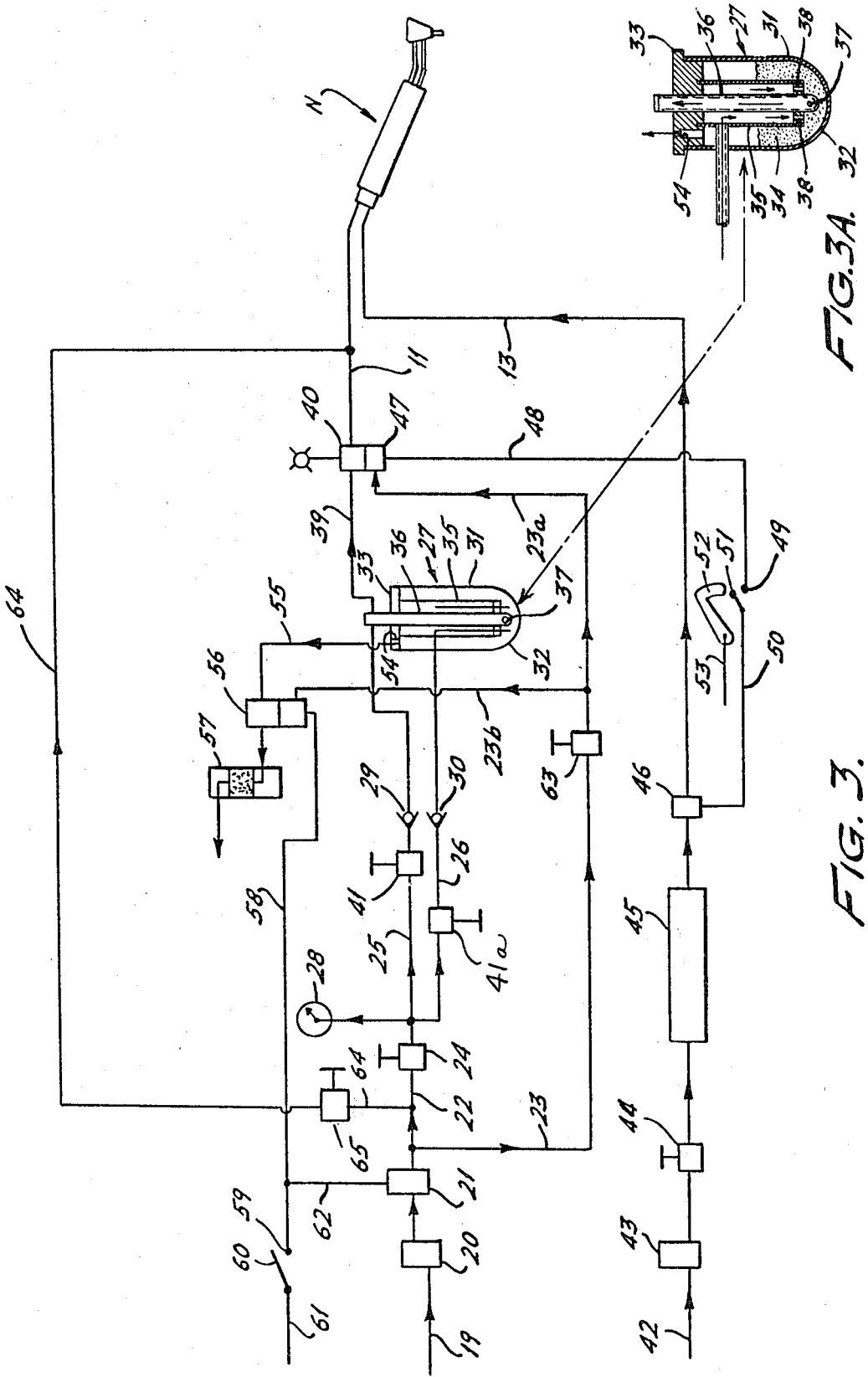

EQUIPMENT AND METHOD FOR DELIVERING AN ABRASIVE-LADEN GAS STREAM

CROSS REFERENCES

This is a continuation of application Ser. No. 65,288, filed Aug. 9, 1979, and abandoned herewith, which is a continuation-in-part of Ser. No. 06/014,435 filed Feb. 23, 1979 and now abandoned, which is a continuation-in-part of Ser. No. 05/928,907 filed July 28, 1978 now U.S. Pat. No. 4,174,571, issued Nov. 20, 1979.

BACKGROUND AND STATEMENT OF OBJECTS

Many forms of devices are known for delivering particles of an abrasive material to a surface to be cleaned or otherwise abraded. Commonly, such devices have a nozzle through which an air or gas stream is delivered carrying particles of the abrasive in suspension, and in general, such nozzles are employed by directing the delivered stream against the surface to be cleaned or abraded. In my prior U.S. Pat. No. 4,174,571 above identified and also in prior U.S. Pat. Nos. 3,882,638 and 3,972,123, water is also delivered from the nozzle, the water stream being in the form of one or more jets arranged so that the water will impinge upon the surface being treated very close to or overlapping with the target area for the abrasive/air stream.

My prior patent identified above discloses the use of a water-soluble abrasive in a system of the kind just referred to, so that when the water stream joins the air/abrasive stream, a slurry is formed and the cleaning or abrasion is effected, at least in part, by means of such slurry.

SUMMARY OF THE INVENTION

The present application is concerned with certain improvements, both in the method and in the equipment, especially adapted for use where the abrasive comprises a water-soluble material. Thus, according to the present invention, a nozzle is provided having delivery passages both for the air/abrasive stream and for the water, the passages being arranged to introduce the water into the air/abrasive stream in a novel manner at the nozzle head immediately upon delivery of the air/abrasive stream and of the water from the respective discharge orifices of the nozzle. Instead of delivering the water as a jet, the water is released as a non-pressurized flow and is caused to join the air/abrasive stream under the influence of the induction effect of the air/abrasive jet.

While certain aspects of the invention are of general applicability, many features of the invention are of special utility in connection with cleaning teeth, particularly cleaning operations involving the use of a powdered water-soluble abrasive delivered to the surfaces of the teeth to be cleaned by a gas stream in which the abrasive particles are suspended. A disclosure of the invention in the present application is therefore made primarily in relation to its application to the field of cleaning teeth.

The invention contemplates a special relationship of the air/abrasive and water passages and orifices which, for reasons which will be fully explained hereinafter, provides for immediate induction of water into the air/abrasive stream just outside the orifice for the air/abrasive stream, so that some of the energy of the air/abrasive stream is imparted to the water, and the water continues with the air/abrasive stream to the target area at a higher energy level. This results in a number of advantages, including more effective cleaning or abrasive action at the target area even at lower pressures. In consequence, cleaning or the desired abrasion may also be effected in a shorter interval of time.

It is also contemplated that the total amount of the abrasive and water delivered to the target area will be such that the water present in the vicinity of the target area will be sufficient to dissolve all of the abrasive delivered, in consequence of which the water will "capture" all of the abrasive particles, thereby virtually eliminating "dusting".

The invention also contemplates employment in combination with the type of nozzle above referred to, of a control system which provides for the "bleeding" of a small amount of air out of the air/abrasive orifice even at times when the normal flow of the air/abrasive stream is shut off, thereby preventing entry of water from the water supply system into the air/abrasive passage in the region of the discharge orifices for the water and the air/abrasive. This is of special importance in the use of water-soluble abrasive particles as is preferred in the practice of the present invention, especially as applied to the cleaning of teeth, because with a water-soluble abrasive, it becomes highly important to preclude any possibility of water or moisture entering into the abrasive handling equipment.

How these and other related objects and advantages are attained will appear more clearly following the description to be given of the accompanying drawings.

BRIEF DESCRIPTION OF DRAWINGS

In the drawings—

FIG. 1 is a view of a handpiece having a nozzle for delivery of the air/abrasive stream and the water stream, constructed in accordance with the present invention;

FIG. 2 is an enlarged fragmentary view of the nozzle structure and somewhat diagrammatically indicating the flow action in the delivery area of the nozzle;

FIG. 3 is a schematic diagram of supply and control equipment which may be used in connection with the handpiece shown in FIGS. 1 and 2; and FIG. 3a is an enlarged detail of the abrasive/air mixing device.

DETAILED DESCRIPTION

Although the equipment and the technique disclosed are adaptable to a wide variety of purposes, in general, the invention is concerned with situations in which relatively mild abrasion is desired, such as is contemplated in dental prophylaxis, including the cleaning of teeth, the removal of stain and of plaque or calculus. Since the equipment and method of the present invention is particularly adapted to the field of dental prophylaxis, the invention is described in that particular environment.

The handpiece comprises a tube 3 by which the instrument is held when in use, for instance in dental prophylaxis. The nozzle head is indicated at 4, and it will be seen that the head is supported in position spaced from one end of the tube 3 by means of a block 5 and the connected tubes 6 and 7.

Tube 6 connects with the central passage and nozzle tube-part 8 in the head, and these interconnected parts 6 and 8 serve to deliver the air/abrasive stream through the nozzle head and out of the discharge orifice.

The tube 7 connects with the annular space between the tube 8 and the surrounding tube 9. This annular space and the tube 7 serve to supply the water desired in the operation of the nozzle.

The air/abrasive mixture is supplied through the connections 10 and 11; and the water is supplied through the connections 12 and 13. Preferably, portions of the supply connections 11 and 13 are flexible, so that the handpiece may be maneuvered and manipulated as required in use of the instrument.

In connection with the following explanation of the operation of the equipment as contemplated according to the present invention, it is first pointed out that as is known, the discharge of a gaseous jet from a nozzle or discharge orifice generates a low pressure area immediately surrounding the discharging gas. This low pressure area is present in the operation of the equipment described and creates what may be termed an ambient induction zone immediately surrounding the jet downstream of the jet discharge orifice.

In consequence of this induction zone, any ambient fluid in the immediate vicinity of the discharging jet will be drawn into the jet flow. Thus, in the equipment as described above in connection with FIGS. 1 and 2, since the annular water supply passage lying between the two nozzle tubes 8 and 9 delivers the water directly into the induction zone surrounding the jet, the wawer is entrained by the jet and some of the energy of the jet is imparted to the water. The water thus proceeds with the jet toward the target area and impinges thereon along with the abrasive particles carried by the jet. For the purposes just mentioned, the outer tube 9 for the water desirably has its discharge orifice located in a plane close to the plane of the discharge orifice of the tube 8 and preferably at least as far downstream as the discharge orifice of the tube 8. Most advantageously, the discharge orifice of the tube 9 is somewhat downstream of the discharge orifice of the tube 8, for instance a distance x—x (see FIG. 2) advantageously from about 0.015" to about 0.032". It will be understood that, depending upon the character of the abrasive and of the operation being performed and further upon the mass of the abrasive and the velocity of the air/abrasive stream, the distance x—x may be varied somewhat from the range indicated.

The flexible tubes 11 and 13 are, of course, extended to the supply and control equipment, one form of which is illustrated in FIG. 3. A line 19 from a source of pressurized air, for instance at from 40 to 80 psi is connected through the filter 20 and the normally closed solenoid shut-off valve 21, with the branch lines 22 and 23. Line 22 is provided with a pressure regulating device 24 which delivers the air through connections 25 and 26 to the abrasive mixing device indicated generally at 27. A pressure gauge 28 indicates the pressure following the reduction of the device 24. The connection 25 is provided with a check valve 29 and the connection 26 with a check valve 30.

The device 27 may be of the type shown in Black U.S. Pat. No. 3,972,123, above referred to, and as seen in FIGS. 3 and 3a, the device 27 includes an outer casing 31 having a rounded bottom 32, and with a removable closure 33 at the top, the casing 31 serving as a reservoir for abrasive particles.

Positioned centrally within the casing 31 is a receptacle or chamber 35 connected with the closure member 33 and projecting downwardly into the casing 31 to provide a central chamber with which the air line 26 connects. Centrally disposed within the container 35 is a hollow tubular member 36 which extends through the closure member 33 and is provided with openings with one of which the air line 25 connects. The lower end of the tube 36 extends through the bottom of the container 35 and projects downwardly below the bottom of the container 35 where the tube is provided with ports 37 for receiving abrasive from the space in the bottom of the outer shell 31. As seen in FIG. 3a, ports 38 in the bottom wall of the container 35 provide for delivery of air from the container downwardly into the mass of abrasive in the bottom of the device, thereby effecting introduction of the abrasive particles from the bottom region of the casing 31 into the tube 36.

In FIG. 3, the delivery line for the abrasive-laden air is indicated at 39 and this line is connected with the interior of the upper end of the tube 36, preferably in line with the air supply connection 25, the line 39 being extended through a valve 40 from which the connection 11 delivers the air/abrasive stream to the handpiece indicated generally at N, as above described in relation to FIG. 1.

The connection 25 is provided with an adjustable needle valve 41 for controlling the amount of air flowing directly to the upper end of the tube 36 of the abrasive mixer. This valve provides for adjustment of the quantity of abrasive picked up by the air stream. When the valve 41 is wide open, a minimum of abrasive will be entrained because the air will readily flow through the line 25 and the connection 39 to the handpiece. As the valve 41 is completely closed, the arrangement then provides for maximum pickup of abrasive, because all of the air reaching the delivery line 39 must pass through the abrasive chamber 35, thereby entraining a maximum of the abrasive. If desired, an adjustable valve 41a may also be provided in branch 26.

When using water-soluble abrasive particles, it is particularly important to provide for airtight sealing of the various parts of the device 27, thereby providing against ingress of ambient air (and thus of atmospheric moisture) into the abrasive supply chamber.

For preventing ingress of moisture into the air/abrasive mixing system, it is also important that the air introduced from supply 19 be substantially dry when water-soluble abrasive is being used. For this, an efficient moisture filter should be employed, for instance in the position of the filter indicated at 20 in FIG. 3. Moisture filters of a variety of types are well-known, some including a device imparting a swirling motion to the incoming air and having a moisture drain for discharging the moisture separately from the air. Some devices of this type even provide for automatic discharge of moisture, but any efficient moisture separator may be used in accordance with the present invention.

Turning now to the water supply system, as shown in FIG. 3, an appropriate water supply line is indicated at 42, this line delivering water through the filter 43 and through a water flow regulating valve 44 to a water heater 45. For dental work, this water heater heats the water to an appropriate temperature for use in the mouth, for instance about 100° F. Desirably, the water heater 45 has some storage capacity, so that a supply of the warmed water will always be available for use. The warmed water flows through the line 13 to the handpiece as shown in FIG. 1, a shut-off valve 46 being provided so that the water flow may be started and stopped at will by the operator.

Turning now to the control system for starting and stopping the abrasive stream and the water flow, it is first pointed out that the valve 40, which may desirably be of the "pinch" valve type is provided with a pneumatic actuating device of known type indicated at 47, this device 47 being supplied with actuating air from the branch 23a of the connection 23 above mentioned. The device 47 is under the control of a solenoid operated by the circuit diagrammatically indicated at 48, which circuit is associated with a contact 49 of a switch device mentioned just below.

The water shut-off valve 46 is solenoid operated and the control circuit for that valve is diagrammatically indicated at 50 as associated with the contact 51 of the main control switch. This main control switch desirably comprises a switch arm 52 connected with a current source 53, the switch arm having a contactor adapted to engage either the contact 51 or both of the contacts 51 and 49. Switches of this type are well known and for dental purposes, are commonly arranged for foot actuation.

With the arrangement just described, the operator in using the equipment will operate the switch arm 52 and this will initially engage the contact 51, thereby opening the water supply valve 46. By further movement of the arm 52, the contact 49 is engaged, thereby opening the valve 40 to deliver the air/abrasive stream to the handpiece. It is advantageous that the switch arm 52 may be operated to initiate substantially concurrently flow of both the water and the air/abrasive stream, but it is preferred to employ an arrangement such as shown, so that water alone may be delivered and also so that whenever abrasive is delivered, there is assurance that water will also be delivered.

The upper portion of the casing 31 of the abrasive mixer (see FIGS. 3 and 3a) is provided with an exhaust port 54 which is connected to atmosphere by the line 55 through a bleed valve 56 and through an abrasive powder trap 57. This valve 56 is normally open and may be of the pinch valve type such as described above with reference to valve 40, the valve 56 being supplied with actuating air pressure through the branch 23b of the line 23, and being under the control of a circuit indicated at 58 which is connected with the contact 59 of a master on-off switch 60. This switch 60 is associated with a power source diagrammatically indicated at 61 and serves not only to operate the valve 56 but further to operate the valve 21 by virtue of the connection 62.

In addition to the branches 22 and 23 of the air inlet system, still another branch 64 is provided having an adjustable flow control valve 65 and extending to join the connection 11 between the handpiece N and the pinch valve 40. The purpose of this connection and its relation to the operation of the handpiece will be explained hereinafter, following the description of the basic operation just below.

When the equipment is to be used, the switch 60 is closed, thereby opening the normally closed solenoid valve 21 and thereby also closing the normally open valve 56. The flow of the air/abrasive and of the water is then manually controlled by the switch 52, which preferrably is a foot switch, in the manner described above. When the equipment is no longer needed for operation, the master switch 60 is opened and the normally closed solenoid valve shuts off the air supply, and in addition, the valve 56 opens to bleed-off of the pressure in the system including the abrasive mixing device, discharge of abrasive particles being prevented by the powder trap 57. This automatic bleed-off of pressure is important particularly for refilling the abrasive casing 31. If the pressure has been exhausted from the system, the removable closure 33 may be separated to permit introduction of a new charge of abrasive.

A valve 63 may be provided to adjust the pressure of the air supplied through the connection 23 to the pinch valves 40 and 56.

The branch line 64 serves an important function in the system, especially in connection with the operation of a handpiece of the kind shown in FIGS. 1 and 2. As above brought out, the orifice for the discharge of the water is at least as far downstream as the discharge orifice for the air/abrasive mixture. With the water supplied from the annular passage immediately surrounding the air/abrasive discharge orifice, in certain positions of the handpiece, and at times when the main control switch 52 is open, there may be tendency for water to dribble into the air/abrasive passage, and this is prevented by the bleeding of air through the branch line 64. Although this feature is of advantage with any type of abrasive, it is particularly desirable when using water-soluble abrasive. In the absence of provision of bleeding of air to the nozzle, partial blocking or irregular operation by virtue of wetted abrasive clogging the air/abrasive passage might occur. However, even with a handpiece having the relationship of air/abrasive and water supply orifices, as disclosed in FIGS. 1 and 2, this problem is eliminated. With constant delivery of some air, preferably a small total flow, through the branch 64 at all times when the master switch 60 is closed, the air delivered through the air/abrasive passage of the nozzle will prevent entrance of the water. The separate flow control valve 65 will serve to adjust this flow to an appropriate value.

In a typical technique using the nozzle and equipment of FIGS. 1, 2 and 3, the air/abrasive stream is delivered at relatively high velocity as compared with the water delivery. Indeed, in the case of the air/abrasive stream, the delivery velocity may range anywhere from several hundred feet per second up to about the speed of sound, i.e., in the neighborhood of 1,080 feet per second; whereas the rate of delivery of the water would ordinarily be only a minor fraction of the speed of the air/abrasive stream, for instance less than half of the velocity of the air/abrasive stream. Indeed, for most purposes and especially when using a nozzle of the kind shown in FIGS. 1 and 2, in which the orifice for the air/abrasive stream is positioned slightly upstream of the annular opening for releasing the water, the water is not actually delivered as a pressurized jet, but is delivered with low velocity flow as a "dribble" or "trickle". Thus, the water is released as an unpressurized flow in a curtain surrounding the pressurized jet of gas and abrasive particles. This assists in providing the desired action of induction of the water by the air/abrasive jet, and the carrying of the water by the jet to the target area.

Another factor to be kept in mind in connection with the operation of the equipment described is the fact that the abrasive particles are preferably soluble in water. As an example, the particles may comprise sodium bicarbonate, sodium glutamate or sodium gluconate, sodium bicarbonate being a preferred material. Although the particle size is not critical, it is preferred for most purposes to employ screened particles of sizes passing through screens in the range from about 140 to 200 mesh. Such particles may range from about 15 to 100 microns. Still further, it is to be kept in mind that the solution of a material of this type in water requires the elapse of a certain solution time; and during the process of dissolving into the water, the abrasive particles form a slurry with the water. I have found that the use of the abrasive material in slurry form carried by the jet is highly effective for various types of dental prophylaxis techniques.

The quantity of water supplied to the jet is preferably in excess of that required to effect complete solution of the abrasive particles, so that the concentration of the abrasive particles will not reach the saturation point in the water. This is desirable in order to insure that when the equipment is being employed in the mouth, all of the abrasive particles will ultimately be dissolved in the water. This insures ready removal, for instance by means of the suction equipment commonly employed in dental work. This factor is also of importance in order to avoid dusting in the mouth, which is objectionable from a number of standpoints, including the comfort of the patient and also in order to avoid objectionable dispersion of dust in the air in the vicinity. The fact that the water is delivered as a non-pressurized flow and is entrained by the air/abrasive stream, is also desirable because this technique facilitates regulation of the water flow rate to the desired value corresponding to the quantity needed to dissolve all of the abrasive and avoid "dusting".

In view of the fact that the instrument or nozzle above described provides for induction of the water into the air/abrasive stream immediately upon discharge of the air/abrasive stream from the nozzle, the stream as it impinges upon the target area actually is a composite comprising the air carrying the abrasive particles and the water in slurry form, which represents a condition of partial solution of the particles in the water. I have found that this is a particularly effective condition for the use of the water-soluble type of abrasive.

The entrainment of the water immediately upon discharge of the air/abrasive jet improves the effectiveness of the cleaning even at lower pressures and this is of significance in reducing splashing and also reducing the potential for damage to the tissues adjacent to the teeth. These factors increase the comfort of the operation from the standpoint of the patient.

Improved cleaning may be effected in shorter time with lower pressures and a given cleaning operation may be performed with a smaller quantity of the abrasive particles, particularly because of the increase in the energy level of the water carried with the stream to the target area.

The nozzle may also be held closer to the target area and this also further diminishes tendency to splashing and permits the use of smaller amounts of water.

The arrangement of the invention also has an important advantage as compared with prior art devices in which water is mixed with abrasive particles within the nozzle passages. Applicant's arrangement eliminates clogging tendencies of such prior art devices.

It is especially to be noted that the water is introduced through an annular orifice immediately surrounding the orifice through which the air/abrasive stream is delivered. Because of the complete encirclement of the air/abrasive stream by the annular water flow, there is virtually no opportunity for any abrasive particles to proceed to the target area in unwetted condition. This is desirable in avoiding dispersion of particles in the environment and also in maximizing the cleaning or abrasive effect.

While, as above indicated, the technique of the present application is particularly adapted for use with water-soluble abrasive particles, certain features, particularly the nozzle structure with the annular water supply passage immediately surrounding the air/abrasive discharge orifice, are also of advantage where non-soluble abrasive particles are employed, because this nozzle arrangement will aid in avoiding "dusting" with either type of abrasive particles.

Although gases other than air may be employed in establishing the abrasive stream, air is the preferred gas for the purpose. It is also possible to employ a liquid other than water, but the preferred technique of the invention requires that the abrasive and the liquid be selected so that the abrasive is soluble in the liquid. Water is preferred for use in the mouth. The quantity of water is most desirably just sufficient to dissolve the quantity of abrasive being delivered.

I claim:

1. A method for effecting abrasion comprising delivering from a nozzle orifice a pressurized jet of particle-laden gas, with resultant development of an ambient induction zone, releasing a substantially unpressurized flow of the liquid into an annual space surrounding the ambient induction zone and thereby establish a combined stream of gas, particles and liquid, and directing the combined stream against the surface to be abraded.

2. A method as defined in claim 1 in which the liquid is released through an annular orifice surrounding the pressurized jet.

3. A method as defined in claim 1 or 2 in which the particles have solubility in the liquid.

4. A method as defined in claim 3 in which the particles are water soluble and the liquid is water.

5. A method as defined in claim 4, wherein the particles have a predetermined solubility in water, and the rate of releasing the water is at least as great as the predetermined solubility so that all of the particles discharged can dissolve in the water, and further comprising directing the combined stream against the surface to be abraded from a distance providing for impingement of the stream upon the surface before complete solution of the particles in the water.

6. A method for effecting mild abrasion comprising generating a stream of a gas laden with a liquid and particles in the liquid some of which are in partially disolved slurry form, and directing the stream against a surface to be abraded, the quantity of the liquid carried to said surface being sufficient to dissolve all of the abrasive material delivered with the stream.

7. A method for effecting abrasion comprising establishing a controllable gas stream, introducing a controllable flow of solid particles into the gas stream, feeding a controllable annular stream of a liquid into a position surrounding the gas stream for induction into the gas stream, and continuing to deliver the stream of gas regardless of the control of the particle introduction.

8. A method as defined in claim 7; and further comprising shutting off the particle introduction while continuing to deliver the stream of gas.

9. A method as defined in claim 7 or 8; and further comprising continuing to deliver the gas stream regardless of the control of the stream of liquid.

10. A method as defined in claim 9; and further comprising controlling the feeding of the liquid stream to shut off the liquid feeding while continuing to deliver the stream of gas.

11. A method as defined in claim 9; and further comprising controlling the gas stream to reduce the gas flow while continuing to deliver the stream of gas.

12. A method for cleaning teeth in a mouth comprising discharging from a nozzle orifice a jet or stream of a particle-laden gas, with resultant development of an ambient induction zone surrounding the jet, feeding an annular stream of liquid into the induction zone, with resultant entrainment of the liquid by the jet, the particles being soluble in the liquid and the rate of feed of the liquid being sufficient to dissolve the particles in the mouth, and directing the liquid-entraining jet against the surface of a tooth to be cleaned.

13. A method for cleaning teeth comprising directing a stream of an abrasive-laden gas toward a target area of the surface of a tooth to be cleaned, concurrently directing a stream of water toward said surface, the abrasive-laden gas being discharged from a nozzle orifice, with resultant development of an ambient induction zone, and the water being fed into said induction zone, with resultant entrainment of the water by the jet, the abrasive comprising solid particles of abrasive material having a predetermined solubility in water, and the rate of feed of the water being at least as great as that corresponding to said predetermined solubility so that all of the abrasive discharged can dissolve in the water fed to said target area, the abrasive/water-laden stream being directed against the surface of a tooth to be cleaned from a distance providing for impingement of the combined stream upon said surface before complete solution of the abrasive particles in the water.

14. A method as defined in claim 13 in which the water is fed in an annular stream surrounding said induction zone.

15. A method as defined in claim 13 in which the stream of abrasive-laden gas comprises a controllably adjustable jet of the abrasive-laden gas and further including delivering a stream of gas into the position of said jet regardless of the adjustment of the abrasive-laden stream.

16. Equipment for delivering a stream of particles for abrasive cleaning comprising, for combination with a supply of particles of dry water-soluble material: an enclosure surrounding the particle supply, means delivering pressurized air to the interior of the enclosure for introducing the particles into a pressurized stream of particles and air, a moisture filter upstream of the air delivered to the enclosure for providing a stream comprising water-soluble particles and substantially moisture-free air, the enclosure being sufficiently airtight to prevent appreciable ingress of ambient air and entrained atmospheric moisture, nozzle means for directing the particle-laden air stream toward the surface to be abraded, nozzle menas for delivering a stream of water into the particle-laden air stream, and a handpiece on which both of the nozzle means are mounted.

17. Equipment for delivering a stream for abrasive cleaning comprising: a nozzle body or head; inner and outer tubular elements mounted on the nozzle head in telescoped relation, the cross-sectional dimensions of said elements providing an annular flow space between the inner and outer elements, and the elements each having an upstream inlet opening and a downstream discharge orifice; adjustable means for delivering a stream of particles suspended in a gas into the inlet end of the inner tubular element for discharge through its discharge orifice, the adjustable means providing for shut-off of the particle-entraining stream, means for filling the annular flow space with a liquid to be delivered from the discharge orifice of the outer tubular element, the filling means comprising means for delivering a supply of such liquid into the inlet end of the outer tubular element; and means for delivering a gas through the inner tubular element when the particle-entraining stream is shut off.

18. Equipment as defined in claim 17 wherein the discharge orifice of the inner tubular element is upstream of the discharge orifice of the outer tubular element; the adjustable means for delivering the particle-entraining stream delivers the stream at a velocity high enough to create an ambient induction zone downstream of the discharge orifice of the inner tubular element; and the liquid filling means delivers the liquid from the discharge orifice as a substantially unpressured flow for induction into the particle-entraining stream in the induction zone.

19. Equipment as defined in claim 17 or 18 wherein the means for delivering a gas when the particle entraining stream is shut off delivers only sufficient gas to keep moisture from entering the inner tubular element.

20. Equipment for effecting abrasion comprising: nozzle means for delivering a pressurized jet of gas laden with particles, with resultant development of an ambient induction zone, and means for delivering a liquid into said induction zone comprising means for releasing a substantially unpressurized flow of the liquid as a continuous liquid curtain surrounding the pressurized jet of particle-laden gas.

21. Equipment for effecting abrasion comprising: a source for supply of water-soluble particles, means for delivering a pressurized jet of a gas, with resultant development of an ambient induction zone, means for feeding particles from said source into said jet, and means for delivering water into said induction zone in a substantially unpressurized continuous curtain surrounding said pressurized jet.

22. A nozzle for delivering a stream for abrasive cleaning comprising: a first, particle-delivery tubular element defining a flow passage for particles suspended in a gas, the flow passage having an orifice for discharging a stream of the gas-suspended particles, and a second, liquid-delivery tubular element surrounding but spaced from the first tubular element for supplying a liquid, the second tubular element being extended slightly beyond the first tubular element.

23. Equipment for delivering a stream for abrasive cleaning, comprising: a nozzle body or head; inner and outer tubular elements mounted on the nozzle head in telescoped relation, the cross-sectional dimensions of said elements providing an annular flow space between the inner and outer elements, and the elements each having an upstream inlet opening and a downstream discharge orifice; means for delivering a pressurized stream of particles suspended in a high velocity gas stream into the inlet end of the inner tubular element for discharge through its discharge orifice, and means for delivering a low velocity flow of liquid into the inlet end of the outer tubular element for discharge through its discharge orifice.

24. Equipment as defined in claim 23 in which the discharge orifice of the inner element is located upstream of the discharge orifice of the outer element.

* * * * *